(12) United States Patent
Goodridge et al.

(10) Patent No.: US 8,754,284 B2
(45) Date of Patent: Jun. 17, 2014

(54) FURTHER IMPROVED BLASTING METHOD

(75) Inventors: Richard Goodridge, Melbourne (AU); Deane Tunaley, Melbourne (AU); Steve Kotsonis, Melbourne (AU); Les Armstrong, Melbourne (AU); Brad Beikoff, Melbourne (AU); Thomas Smylie, Melbourne (AU)

(73) Assignee: Orica Explosives Technology Pty Ltd, Melbourne (AU)

( * ) Notice: Subject to any disclaimer, the term of this patent is extended or adjusted under 35 U.S.C. 154(b) by 928 days.

(21) Appl. No.: 12/232,825

(22) Filed: Sep. 24, 2008

(65) Prior Publication Data

US 2012/0282680 A1 Nov. 8, 2012

(30) Foreign Application Priority Data

Feb. 1, 2008 (AU) ................................ 2008900469
Sep. 19, 2008 (AU) ................................ 2008904879

(51) Int. Cl.
| | | |
|---|---|---|
| *A62D 3/30* | (2007.01) | |
| *F27B 14/10* | (2006.01) | |
| *C06B 21/00* | (2006.01) | |
| *F42B 33/06* | (2006.01) | |
| *F42B 3/192* | (2006.01) | |
| *F42D 5/04* | (2006.01) | |
| *A62D 3/02* | (2007.01) | |
| *C02F 3/34* | (2006.01) | |
| *C12N 15/82* | (2006.01) | |

(52) U.S. Cl.
CPC ............. *C06B 21/0091* (2013.01); *F42B 33/06* (2013.01); *F42B 3/192* (2013.01); *F42D 5/04* (2013.01); *A62D 3/02* (2013.01); *C02F 3/342* (2013.01); *C12N 15/8259* (2013.01)
USPC ............ 588/313; 588/401; 588/403; 432/262

(58) Field of Classification Search
CPC ........ B09C 1/10; B09C 1/15; C06B 21/0091; F42B 33/06; F42B 3/192; F42D 5/04; A62D 3/02; C02F 3/342; C12N 15/8259
USPC ......... 210/602, 743, 202, 206, 259, 611, 688, 210/757; 588/403, 318, 306, 313, 317, 320, 588/401, 406–409; 435/128, 262.5
See application file for complete search history.

(56) References Cited

U.S. PATENT DOCUMENTS 5,928,859 A * 7/1999 Nicklin et al. .................... 435/4
6,120,627 A * 9/2000 Badger et al. ............... 149/108.8

\* cited by examiner

*Primary Examiner* — Jennifer A Smith
(74) *Attorney, Agent, or Firm* — Birch, Stewart, Kolasch & Birch, LLP

(57) ABSTRACT

The present invention relates to a method of deactivating an explosive composition in order to render the composition safe. The present invention also relates to a cartridge that contains an explosive composition and that is adapted to achieve deactivation of the explosive composition in the event that it is not detonated as intended during use.

14 Claims, 7 Drawing Sheets

FURTHER IMPROVED BLASTING METHOD

The present invention relates to a method of deactivating an explosive composition in order to render the composition safe. The present invention also relates to a cartridge that contains an explosive composition and that is adapted to achieve deactivation of the explosive composition in the event that it is not detonated as intended during use.

Explosives are used in a significant number of commercial applications, such as mining, quarrying and seismic exploration. In mining and quarrying a detonator is typically used to initiate a cartridged primer charge that in turn detonates bulk explosive. In seismic exploration a relatively small cartridged explosive charge is initiated using a detonator and the shock waves that are generated are monitored and analysed.

When a charge fails to detonate as intended there are obvious safety and security issues. In that event, it may be possible to recover the charge, although this is not always possible for a variety of reasons. For example, in seismic exploration where charges or trains of charges are positioned and detonated, recovery of undetonated charges can be difficult, especially when the charge(s) is/are positioned in an underground borehole and the borehole has been backfilled, as is common practice. There are therefore instances where undetonated charges remain unrecovered in the field. In such cases, and as a general point, it would therefore be desirable to render safe any undetonated and unrecovered explosive charges. A variety of approaches to address this need already exist.

By way of example, U.S. Pat. No. 3,948,177, describes an explosive cartridge for underwater blasting which is said to be self-disarming in the event of an underwater misfire. The cartridge comprises a closed shell including an internal conduit. Water external to the cartridge is prevented from flowing into the conduit by a watertight seal. The force of a percussion impact initiation can however break the watertight seal thereby allowing water to flow into the conduit and contact with explosive composition contained. In turn, water can dissolve the (nitrocarbonate) explosive possibly also causing it to flow out of the body of the cartridge. The result is desensitisation. Whilst generally useful, a problem with this approach is that desensitisation is contingent upon some form of specific force associated with a misfire to break the watertight seal. If there is no applied force resulting from a misfire, the cartridge would not be disarmed by the action of water.

Other approaches, such as those described in WO 97/19253 and WO 98/55822, rely on the use of micro-organisms to effect bio-remediation of an explosive composition in the event that the composition is not detonated as intended. However, being biological in nature, care needs to be taken to provide the micro-organisms in a form that is active or potential to be active, and care needs to be taken not to destroy the micro-organism thereby rendering them useless. It will also be necessary to supply micro-organisms with suitable nutrients/metabolites in order to sustain them when they are required to be active. Approaches using micro-organisms may also lead to unwanted introduction or leakage of possibly exotic micro-organisms and/or chemicals into the environment. Thus, the use of micro-organisms in this context is not without practical problems.

The present invention seeks to provide an alternative approach to rendering safe explosive compositions that does not suffer the disadvantages described above.

Accordingly, in one embodiment, the present invention provides a method of deactivating an explosive composition provided in an explosive cartridge, which method comprises exposing the explosive composition to a deactivating agent that renders the explosive composition insensitive to detonation. In the present invention, and as will be explained in more detail below, the deactivating agent is an enzyme. The enzyme is used in isolation from any living cell with which it might normally be associated or produced. Unless otherwise stated the term deactivating agent is used to denote such enzymes. Mixtures of enzymes may be used.

This definition is intended to embrace naturally occurring or produced enzymes that have been isolated or extracted and synthetic enzymes.

In accordance with the present invention, the action of a deactivating agent on the explosive composition is responsible for rendering the explosive composition insensitive to detonation, i.e. safe. Herein, unless otherwise evident, when it is indicated that an explosive composition is rendered insensitive to detonation means that the explosive composition has, by action of the deactivating agent, been desensitised at least to the extent that the normal (predetermined) method of initiation of the explosive composition is no longer effective. Thus, for an explosive composition that is known to be detonated using a particular type of initiating device, in accordance with the present invention the explosive charge is rendered insensitive to detonation if it is no longer possible for it to be initiated in that way. The fact that an explosive composition has been rendered insensitive to detonation does not mean that the explosive charge is completely undetonable (although this is of course a possibility). At the very least, the extent of desensitisation effected by the deactivating agent in accordance with the invention results in the explosive composition being insensitive to the initiation means that was otherwise and originally intended to cause detonation of the explosive composition.

In an embodiment of the present invention, as well as deactivating the explosive composition, the enzyme converts the explosive composition (or components thereof) into one or more compounds that are more environmentally acceptable.

When the enzyme is derived from a living cell it may be derived from a microorganism, animal or plant cell. Microorganisms capable of degrading explosive material are known in the art and to the extent that this activity is attributed to enzymes associated with or produced by the microorganism, the microorganism may be a useful source of enzymes for the present invention. Examples of microorganisms that are known to exhibit that ability include *Pseudomonas* spp., *Escherichia coli, Morganella morganii, Rhodococcus* spp., *Comamanos* spp., and denitrifying bacteria. Suitable *Pseudomonas* spp. microorganisms include microorganisms in the group *aeruginosa, fluorescens, acidovorans, mendocina, cepacia.*

The enzymes used in accordance with this embodiment must be functional under the conditions of intended use.

In the invention the enzyme(s) are used in isolation from the cells that otherwise produce or are associated with the enzyme(s). In this case the enzyme is provided in a substantially purified form or in a cell-free form. The latter may be a cell free extract or the enzyme may be provided as a component of a cell-free composition. The enzyme may be produced and isolated by conventional techniques. Enzymes that are known to be useful in degrading explosive materials are known in the art. As an alternative the enzymes may be synthetic and thus not derived from living cells It is also known that certain plants have a phytoremediating/rhizoremediating effect on explosive materials. To the extent that this effect is due to enzymes that are produced by or associated with the living cells of the plant, the plant may be a useful source of enzymes for the present invention.

Laundry and dishwasher detergents may include suitable enzymes for use in the present invention and the detergent may represent a convenient format in which the enzyme is provided into the explosive cartridge. In this embodiment it may be appropriate to provide the enzyme with co-factors and the like that are required for the relevant functionality. Temperature and pH conditions may also need to be taken into account.

Typically, the deactivating agent will itself cause suitable desensitisation of the explosive composition. However, it is also possible that further desensitisation may be achieved through the combined activity of the deactivating agent and another reagent useful in deactivating the explosive composition. The another reagent may be a microorganism, (non-biological) chemical, and/or a plant or plant extract/derivative. In the following, unless context requires otherwise, reference to an enzyme/deactivating agent may be taken as reference to the combined use of the enzyme/deactivating agent and the another reagent.

In one embodiment the another reagent may be a reagent external to the explosive cartridge that will find its way or be introduced into the cartridge during use thereof and that can contribute to desensitisation of the explosive composition. Such reagents may be naturally present in the environment in which the explosive cartridge is to be used. In this embodiment the explosive cartridge will be adapted to allow the relevant reagent to be introduced into or enter the explosive cartridge as required. By way of example, the explosive cartridge may be designed to allow environmental water to enter the body of the cartridge and contact the explosive composition, assuming of course that water has a desensitising effect on the emulsion.

By way of further example, the cartridge may be adapted to allow ingress of naturally-occurring microorganisms (or other remediating agent(s)), for example water-borne microorganisms, that exist naturally in the environment in which the explosive cartridge is being used and that are capable of remediating the explosive composition contained in the cartridge. The cartridge may be provided with a nutrient source to promote uptake and proliferation of such microorganisms (or agent(s)). In this case water serves as a vehicle that transports the microorganisms into contact with the explosive composition.

Central to the present invention is the nature of the deactivating agent and its use in the context of desensitising an explosive composition provided in an explosive cartridge. In certain embodiments of the invention the explosive cartridge may be of known design. For example, the explosive cartridge may comprise a reservoir (or chamber) in which the deactivating agent is provided and a separate component, typically in the form of a shell (or cartridge,) in which the explosive composition is provided. The reservoir and shell are adapted to be connected to each other. The act of connecting the reservoir to the shell may cause release of the deactivating agent from the reservoir so that the deactivating agent comes into contact with the explosive composition. In another embodiment valve means may be provided between the reservoir and shell, as part of one or both components, to regulate when release of deactivating agent takes place. This type of arrangement is disclosed, for example, in U.S. Pat. No. 5,736,669 and U.S. Pat. No. 5,763,815, the contents of which are incorporated by reference.

In another embodiment the deactivating agent and explosive composition may be provided adjacent to each other but contact of them is prevented by use of a physical barrier element. Prior to use of the explosive cartridge, that is positioning and priming of the explosive cartridge, the barrier element prevents contact between the deactivation agent and explosive composition. In embodiments of the present invention the barrier element is breached or removed instantaneously when the explosive cartridge is being used in the field. In other embodiments the barrier element remains in place between the deactivating agent and explosive composition when the explosive cartridge is actually positioned and primed but some mechanism for delayed removal of the barrier element is activated. The barrier element may be breached/removed by chemical, mechanical or electrical means. Mechanisms useful in implementation of this embodiment of the invention are known in the art, for example from U.S. Pat. No. 6,120,627, U.S. Pat. No. 6,660,112, U.S. Pat. No. 6,644,200 and U.S. Pat. No. 7,077,044, the contents of which are incorporated by reference.

Typically, the external configuration of the explosive cartridge is cylindrical with the deactivating agent and explosive composition occupying respective chambers within the body of the cartridge. In this embodiment the explosive cartridge is invariably sealed so that there is no risk of escape of components, for example, during storage and/or transportation. Sealing may be achieved by conventional techniques depending upon the materials used to form the cartridge. If the cartridge is formed from plastic, the body of the cartridge, including the respective chambers of it, may be formed by injection moulding with the chambers of the cartridge being loaded with the deactivating agent and explosive composition as required, with subsequent sealing (heat sealing, for example) in order to seal the inlets through which these components are supplied into respective chambers in the body of the cartridge.

The cartridge may be made up of independent components that are adapted to be attached to each other as the cartridge is being loaded with respective components and when used in the field. By way of example, the explosive composition may be provided in a chamber that is adapted to be secured to another component comprising a chamber for the deactivating agent. The chamber for the deactivating agent may be of single piece construction, for example formed by injection moulding of a suitable plastics material, and include at least one detonator receiving channel as part of the construction. The chamber for the deactivating agent may be provided as part of a cap well or lid piece for the chamber housing the explosive composition. The individual components may be attached to each other by any suitable mechanism, such as interference (friction) fit, male-female screw threading or clip fitting. In this case the explosive composition may be loaded into the respective chamber and the lid secured to the top of the explosive composition chamber. If the explosive composition is a fluid, the attachment must be such that loss of explosive composition is prevented. However, if the explosive composition is solid in nature, for example when the explosive composition is cast hot and allowed to solidify, the attachment may be loose fitting, and this may be beneficial in terms of allowing water to enter the cartridge, as will be explained. The cap well (lid piece) will also generally include a lid/seal over its open end, and this may also allow water to enter the cartridge. As a further alternative, rather than relying on separate chambers that are integrally formed as parts of the cartridge structure, the deactivating agent and/or explosive composition may be provided in independent containers that are inserted into a rigid cartridge body. In this case it will be appreciated that the cartridge is made up of at least two independent parts and that in use the cartridge is assembled from those parts.

The material(s) used to form the cartridge of the invention should not be corroded by or be reactive towards the deactivating agent and explosive composition to be contained. Thus, the cartridge will retain its structural integrity.

In one embodiment the barrier element takes the form of an internal wall or internal wall portion (membrane) separating the chambers containing the deactivating agent and explosive composition. When this wall or wall portion is breached or removed the deactivating agent and explosive composition come into direct contact with each other. In accordance with the invention, this occurs only during use. Thus, in one embodiment the wall or wall portion may be ruptured by insertion of a detonator into the explosive cartridge (detonators are invariably used to initiate detonation), or by the act of connecting one cartridge to another to form a train of cartridges, as is common practice.

With respect to use of a detonator, the cartridge is usually adapted to receive the detonator in a suitably shaped passage extended axially within the body of the cartridge. The cartridge may be adapted to receive a single detonator or more than one detonator in respective, suitably shaped passages. In this regard it should be understood that explosive cartridges for use in seismic exploration, for example, generally allow inclusion of two detonators, a primary detonator and a secondary (back-up) detonator in case the primary detonator does not detonate as intended.

In the embodiment described above the barrier element may extend across this detonator-receiving passage such that, when the detonator is pushed into position in the cartridge, the wall originally separating the deactivating agent and explosive composition is ruptured thereby allowing these components to come into direct contact with each other. Alternatively, the action of inserting the detonator into the cartridge may cause a separate component to rupture the wall. This component may be a needle-like structure, rigid tube, or similar.

To achieve release of the deactivating agent when cartridges are coupled together in a train, the lower end of the cartridge may include a suitably shaped extension for insertion into the detonator-receiving passage of an adjacent cartridge (of the same design). Insertion of this extension into the detonator-receiving passage has the same effect as inserting a detonator in that the wall/membrane separating the deactivating agent and explosive composition is ruptured. Alternatively, the upper end of the cartridge may include a component that is adapted to be displaced downwardly (or upwardly) when the cartridges are coupled together and that causes the wall membrane to be ruptured. To facilitate attachment explosive cartridges in accordance with the present invention may also include suitable engagement or retaining means. For example, the lower end of the cartridge may include external threads with the upper end including corresponding internal threads thereby allowing adjacent cartridges to be secured to each other. It will be appreciated that the external shape of the lower end of the cartridge is adapted to mate with the upper end of an adjacent cartridge. In the particular embodiment described, the act of engaging and screwing cartridges together may cause rupture of the wall.

In another embodiment the deactivating agent and explosive composition may be provided in separate (sealed) components that are coupled only when the cartridge is to be used. Thus, the deactivating agent may be provided in a sealed cap that is adapted to be attached to a base cartridge portion including the explosive composition. The act of coupling the components together may cause release of the deactivating agent and this may be achieved along the lines already described. In this embodiment the cap containing the deactivating agent may need to be adapted to allow for a detonator to be inserted into the base cartridge portion. Additionally, a train of cartridges would need to be constructed with a cap containing the deactivating agent provided immediately above each base cartridge portion. Construction of a train of individual explosive charges may be more onerous in this embodiment when compared with embodiments where the deactivating agent and explosive composition are provided in a single (cartridge) structure.

Irrespective of which particular embodiment is employed, the integrity of the barrier element will only be compromised when the detonator is being used in the field. Prior to that point in time the barrier element is intended to remain intact thereby separating the deactivating agent and explosive composition.

In the embodiments described, when breach or removal of the barrier element is instantaneous, the deactivating agent and explosive composition will come into contact with each other straightaway. In this case the deactivating agent will start acting upon the explosive composition immediately. However, in such embodiments for the explosive cartridge to have a period of usefulness, it is important that the deactivating agent does not render the explosive composition insensitive to detonation, or reduce significantly the energy output of the explosive composition, immediately. If it did, the explosive cartridge would be useless, or of little practical use, as soon as the deactivating agent is released from the chamber containing it. It is instead intended that the deactivating agent desensitises the explosive composition after a suitable period of time and by this is meant a period of time after which detonation should otherwise have occurred. Thus, after release of the deactivating agent, the explosive cartridge may need to remain fully detonable (with the energetic output of the explosive composition unaffected or substantially unaffected) for a period of up to a few weeks, preferably for a period of up to a few (e.g. three to six) months. In some instances the explosive cartridge may be required to remain detonable (and useful) for a longer period, for example up to about twelve months. The reaction kinetics associated with the deactivating agent and explosive composition will dictate the rate of which the explosive composition is desensitised. In practice to achieve a useful product the reaction is relatively slow so that the transition between the explosive composition being detonable and non-detonable may be a relatively long one.

In other embodiments of the present invention the barrier element is adapted/designed to be breached or removed only after the explosive cartridge is used. In these embodiments removal/breach of the barrier element is not instantaneous on use of the cartridge, but rather some mechanism is activated that will lead to removal/breach of the barrier element after some predetermined period of time. Taking into account the activity of the deactivating agent this will invariably be a period of time after which desensitisation of the explosive composition is desired due to failure of the explosive cartridge to be detonated, as described above. The mechanism by which the barrier element is removed or breached may be chemical, electrical or mechanical in character.

In another embodiment of the invention the deactivating agent is provided separate to the explosive composition and must be mobilised in order for contact with the explosive composition to take place. In this case the deactivating agent may be provided in any suitable form that is rendered mobile by water that enters or is delivered into the explosive cartridge when used. Thus, the deactivating agent may be provided in dehydrated or dried form such that contact with water results in formation of a solution or suspension of deactivating agent in water. Formation of the solution or suspension renders the deactivating agent mobile. The deactivating agent may also be provided as a gel or viscous liquid that itself is not suitably mobile but that when contacted with water becomes mobile. Herein reference is made to water being used as the vehicle that renders the deactivating agent mobile. Other liquid vehicles may of course be used. Water tends to be convenient as it is generally present in environmental in which the explosive cartridge will be used.

A water-permeable membrane may be used to separate the explosive composition and deactivating agent with the deactivating agent permeating this membrane when mobilised by contact with water. In this regard the water-permeable membrane may be provided with one or more apertures to allow the (mobilised) deactivating agent to come into contact with the explosive composition. The same apertures may also allow water to come into contact with the deactivating agent in order to render it mobile. It may also be possible to implement this embodiment using a water-degradable membrane to separate the explosive composition and deactivating agent. In this case the deactivating agent may be provided in a water-degradable (or water-soluble) packet or wrapper, formed for example from polyvinyl alcohol. This may simplify design since in this case the encapsulated deactivating agent may simply be positioned on top of or within the bulk of the explosive composition. In these embodiments it is important that the membrane or packet/wrapper that is used is not degraded by the explosive composition.

In this embodiment the explosive cartridge may include one or more inlets (apertures) and/or water-degradable pathways to allow environmental water to flow into the cartridge and directly into contact with the deactivating agent. Additionally, or alternatively, the explosive cartridge may include one or more inlets (apertures) and/or water-degradable pathways to allow environmental water to flow into the cartridge and into contact with the deactivating agent through the explosive composition. In this case the explosive composition may include channels to allow water to migrate to the deactivating agent. The channels may be artificially formed in the explosive composition and/or be naturally occurring given the nature of the explosive composition and the manner in which the explosive composition is loaded into the explosive cartridge. With respect to the latter case, if the explosive composition is delivered into the respective chamber above its melting point and is allowed to solidify subsequently, a network of cracks and fissures may be formed in the solidified form of the explosive composition. Water may migrate through these cracks and fissures. In this embodiment water must obviously be able to enter the explosive composition in the first place, and ways in which this can be achieved are described herein. When a water-permeable or water-degradable membrane is used to separate the explosive composition and deactivating agent, the membrane may define a cavity or cavities that separate(s) the deactivating agent and explosive composition with environmental water entering these cavities when the explosive cartridge is used. As a further variation, water may be supplied into the explosive cartridge immediately prior to use. For example, an explosive cartridge could be suitably submerged in water prior to being positioned in a blasthole or the like, so that the water enters the explosive cartridge as desired. Water may also be delivered into the explosive cartridge through a feed line.

In another related embodiment water or some other suitable solution may be contained in a membrane within the shell of the cartridge and/or the explosive composition, with the membrane releasing the water/solution after some predetermined time.

In a further embodiment the deactivating agent may be provided in contact with the explosive composition, for example the deactivating agent may be distributed through the bulk of the explosive composition. In this embodiment the deactivating agent may be encapsulated or provided in pelletised or granulated form, or the like. This general approach is known in the art in relation to the use of microorganisms as deactivating agent, for example from U.S. Pat. No. 6,334,395 and U.S. Pat. No. 6,668,725.

This embodiment also relies on the need for the deactivating agent to be in contact with water so that it is in a form that will effect desensitisation and/or so that it is in a form suitably mobile to effect desensitisation. As noted above the explosive cartridge may include one or more inlets or water-degradable pathways to allow the introduction of water into the body of the cartridge. Water may be conveyed to, and possibly through the bulk of, the explosive composition by use of a suitably designed water-permeable or water-degradable membrane. The explosive composition may be housed in a chamber (shell) the outer walls of which are formed from a water-permeable cardboard or plastics-based material. When the explosive composition is a solid, such as cast Pentolite, in principle it may be possible to dispose of any outer shell. However, the end of the explosive cartridge may then require a rigid end cap or similar housing to facilitate loading of the cartridge into a blasthole.

In an embodiment of the present invention the explosive composition is deactivated by the combined activity of the deactivating agent as described herein and an additional deactivating agent that enters the explosive cartridge during use thereof. For example, the additional deactivating agent may be at least one microorganism that is present in the environment in which the explosive cartridge is being used and that is capable of acting on the explosive composition in order to convert it into by-products that are at least less detonable, and preferably non-detonable, when compared with the explosive composition in its original form in the explosive cartridge.

In an embodiment of the invention the additional deactivating agent acts on the explosive composition to render it more environmentally friendly (non-toxic), as might be useful in practice.

In this embodiment the at least one microorganism may be carried into the explosive cartridge in water present in the surroundings in which the cartridge is positioned (blastholes are typically wet environments). The cartridge may be designed to include apertures or inlets to allow ingress of environmental water, and thus microorganisms, into the body of the cartridge and into contact with the explosive composition. Channels may be provided in and/or around the explosive composition to ensure a suitably high surface area of contact between incoming water/microorganisms and the explosive composition.

In one embodiment the cartridge may include a water-permeable or water-degradable outer shell (membrane) surrounding the explosive composition, possibly with channels or passages extending into the explosive composition. In use water permeates or degrades the shell (and channels/passages when present) thereby allowing the water and microorganisms to come into contact with the explosive composition. At that time the microorganisms begin to act on the explosive composition as intended.

In another related embodiment the cartridge includes a shell and optionally channels/passages formed of a material that will be dissolved by water and/or consumed by microorganisms present in the environment in which the cartridge is used. In this embodiment the microorganisms also have the ability to act on the explosive composition as described above. Desirably the microorganisms have a greater affinity for the material of the shell (and where present channels/ passages) so that once the material is breached the microorganism acts on the explosive composition.

In these embodiments the time taken for the microorganism to come into contact with the explosive composition and the rate at which the microorganism acts on the explosive composition as desired (under prevailing conditions of use) is such that deactivation of the cartridge will not be achieved until a predetermined amount of time has elapsed, prior to which the cartridge would normally have been detonated.

The explosive composition used in the explosive cartridge of the invention is conventional in nature and will be selected based on its ability to be desensitised by the deactivation agent or agents to be used. Examples of explosive materials that may be considered for use in the present invention include trinitrotoluene (TNT), pentaerythritol tetranitrate (PETN), cyclotrimethylene trinitramine (RDX) and cyclotetramethylene tetranitramine (HMX). The explosive composition may be an emulsion explosive, a water-gel explosive or an ANFO or other nitrate-based composition. Other less conventional explosives may also be used such as liquid or gel compositions which are aqueous or non-aqueous and possible containing other explosive components such as perchlorates. Combinations of explosive materials may also be used. For example, the explosive composition may be Pentolite, a mixture of PETN and TNT. The explosive composition may also contain other explosive and/or reactive ingredients, such as RDX and metallic (e.g. aluminium) particles.

In one embodiment of the present invention the explosive composition may be a water-in-oil emulsion. Emulsion explosive compositions typically includes a discontinuous phase comprising a supersaturated aqueous solution of an oxidiser salt (usually ammonium nitrate) dispersed in a continuous oil (fuel) phase. Such emulsions are usually formed by mixing the components in the presence of a suitable emulsifier. In the context of emulsion explosive compositions, the deactivating agent may include any reagent that is capable of breaking, or rendering unstable the emulsion, thereby causing it to be insensitive to detonation. Usually, the deactivating agent will have the effect of causing crystallisation of the supersaturated emulsion component (the oxidiser salt in the type of emulsions described). Accordingly, one skilled in the art may select suitable reagents for use as deactivating agent, at least for initial screening, based on a general knowledge of emulsion chemistry and of reagents that are known to cause unwanted crystallisation of (supersaturated) emulsion explosive compositions. Here it is important to note that the present invention seeks to make positive use of reagents that might previously have been regarded as being detrimental in the context of emulsion explosive compositions. The type of deactivating agent used will usually be selected on the basis of the emulsion explosive composition being used rather than vice versa.

The present invention has particular utility in seismic survey applications and in this case the explosive cartridge takes the form of a seismic charge. One skilled in the art will be familiar with the type of explosives in this context.

Embodiments of the present invention are illustrated in the accompanying non-limiting figures, in which.

Figure 1:
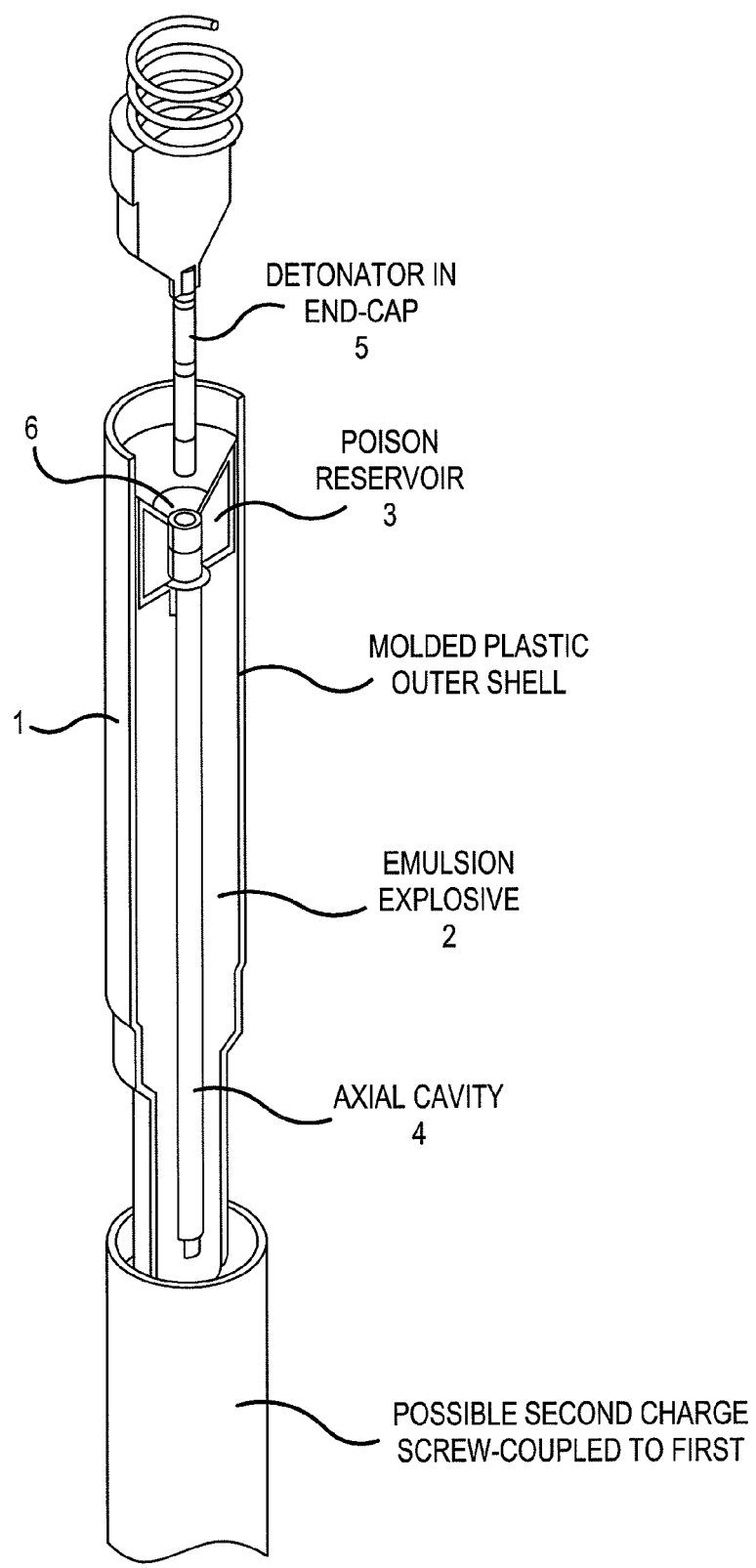
FIGS. 1-3 shows a cross-section of explosive cartridges in accordance with the present invention, with FIGS. 2 and 3 illustrating the same design.

Thus, FIG. 1 shows an explosive cartridge (1) suitable for use in seismic exploration. The explosive composition and deactivating agent remain sealed in their respective chambers (2, 3). Therefore, subject to the stability of the emulsion explosive composition, the cartridge (1) is a storage stable product.

The cartridge also includes a small diameter axial channel (4) extending down within the body of the cartridge (1) from the deactivating agent chamber (3) through the explosive composition. This channel (4) is defined by a wall formed from a polymeric material that is degradable on contact with the deactivating agent. In the arrangement shown in FIG. 1 the channel (4) is empty since the deactivating agent has not been released from the chamber (3). A seal (not shown in detail) is provided between the deactivating agent chamber (3) and the channel (4), this seal being designed so that breakage of it will cause release of deactivating agent from chamber (3) into channel (4) extending through the explosive composition.

The upper end of the cartridge (1) is adapted to receive a cylindrical detonator (5). When the cartridge (1) is to be used in the field, this detonator (5) is inserted into a detonator-receiving channel (6) extending into the body of the cartridge (1). In the embodiment shown the detonator-receiving channel (6) is provided as an extension of the channel (4). The action of inserting the detonator into the detonator-receiving channel (6) causes the seal between the deactivating agent chamber (3) and the channel (4) to be broken thereby releasing deactivating agent into the channel (4). However, contact between the deactivating agent and the explosive composition is prevented by the walls of the channel (4) and the deactivating agent must first penetrate these walls before contacting explosive composition.

Although not shown, it may be necessary for the design to include some kind of air inlet (or breather tube) to allow air into the deactivating agent chamber (3) as deactivating agent flows out. In the absence of an air inlet, flow of deactivating agent may be restricted. Generally, air will only be allowed into the deactivating agent chamber (3) when the cartridge is being used, thereby preventing leakage of the deactivating agent.

Surface tension effects of the deactivating agent may also influence design or the characteristics of the deactivating agent to be used. Although also not shown it may be useful to allow the deactivating agent once released to come into contact with a wick or open cell foam that extends down into the channel (4) and that has the effect of conducting/drawing deactivating agent down into the channel (4).

The walls of the channel (4) are made of a degradable (polymeric) material that may be hydrolysed by water present in the aqueous deactivating agent. On contact of the deactivating agent and the walls of the channel (4) the deactivating agent therefore (slowly) degrades the walls. Whilst the walls remain intact no contact of the deactivating agent and explosive composition takes place and this delay allows a user of the cartridge (1) sufficient time to load the cartridge into a blasthole and attempt detonation of the cartridge (1) as intended. Thus, the functionality of the cartridge (1) remains intact even though the deactivating agent has been released from the chamber (3) originally containing it.

After a predetermined period of time (usually selected to be a number of months) the walls of the channel (4) will have been dissolved/consumed/weakened by the deactivating agent. The integrity of the walls is therefore lost and the deactivating agent comes into contact with the explosive composition.

Although not shown in FIG. 1 the lower end of the cartridge (1) may also be shaped in order to be inserted into the detonator-receiving channel of an adjacent cartridge. Thus, forming like cartridges into a train of cartridges can also result in release of deactivating agent from the chamber (3) in which it is originally contained. The upper and lower ends of the cartridge (1) may also contain cooperating features, such as screw threads, to enable cartridges to be secured together.

In the embodiment described when released the deactivating agent flows into channel (4) running essentially the entire length of the explosive composition included in the cartridge (1). This is a preferred arrangement and the volume of the cavity is configured to be such that in use it will contain sufficient deactivating agent to deactivate the entirety of the explosive composition (over time). After the wall of the channel (4) has been broken down by action of the deactivating agent, explosive composition adjacent to the deactivating agent and thus adjacent to the detonator when positioned in the cartridge will be first exposed to the deactivating agent. This region of the explosive composition therefore comes into contact with the highest concentration of deactivating agent thereby promoting the fastest and most effective deactivation of the explosive composition. Other arrangements are of course possible.

In an alternative arrangement the deactivating agent flows into an annular cavity provided in the outer periphery of the cartridge body. In this embodiment it will be appreciated that the degradable material is provided on the outer surface of the emulsion preventing contact between the explosive composition and the deactivating agent (when released). When the material is degraded by the deactivating agent, the deactivating agent will contact outer regions of the explosive charge first. However, assuming the cartridge is used with a detonator in a central detonator-receiving passage, this embodiment suffers the potential drawback that explosive composition far removed from the location of the detonator will be deactivated first. There is therefore a greater risk of failure to deactivate the explosive composition if the deactivating agent action does not penetrate radially into the explosive composition (towards the location of the detonator). This embodiment does however have the advantage of a high surface area of contact between the deactivating agent and explosive composition.

As a further alternative, the deactivating agent may flow into a cavity provided over the top of the body of explosive composition provided in the cartridge. However, this embodiment suffers the potential disadvantage of low surface area of contact between the deactivating agent and explosive composition and this can lead to slow and/or incomplete deactivation of the explosive composition. Other alternatives are of course possible within the context of the present invention.

Figure 2:
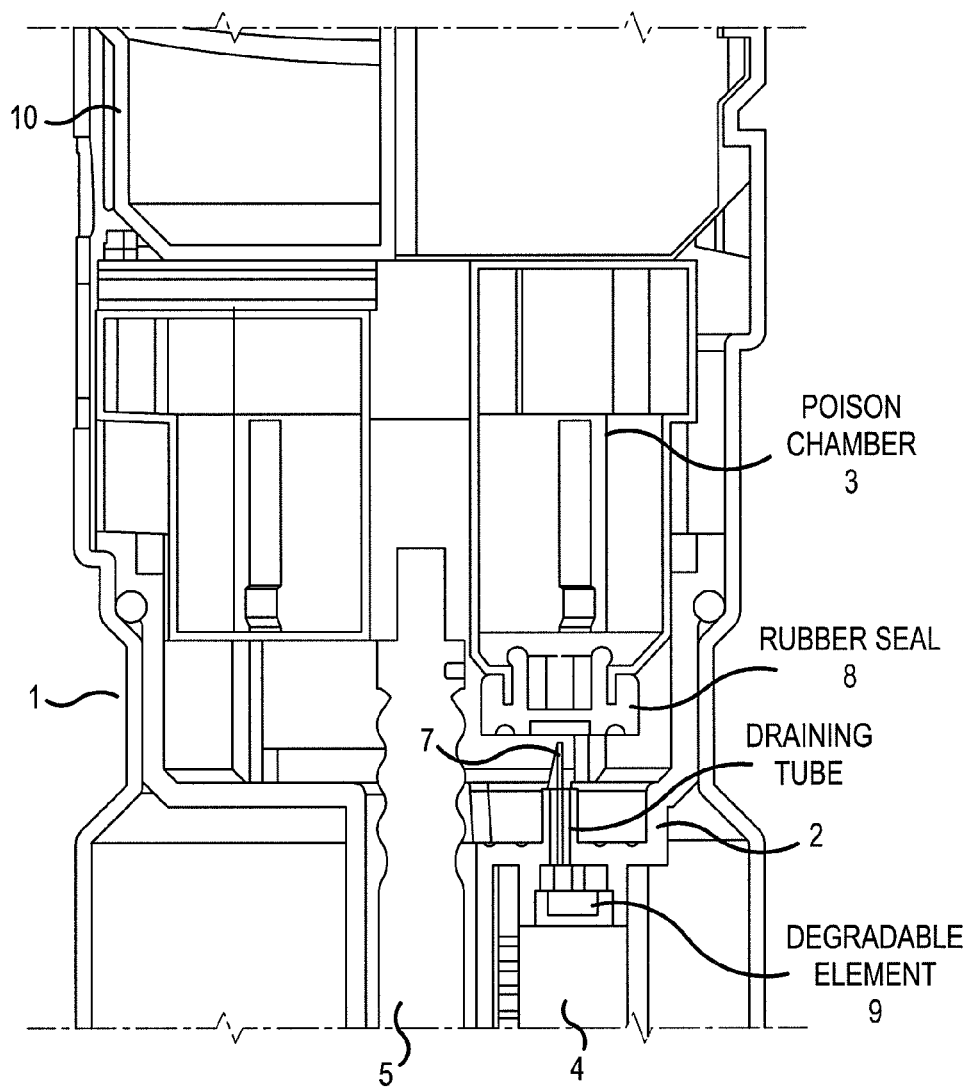
Figure 3:
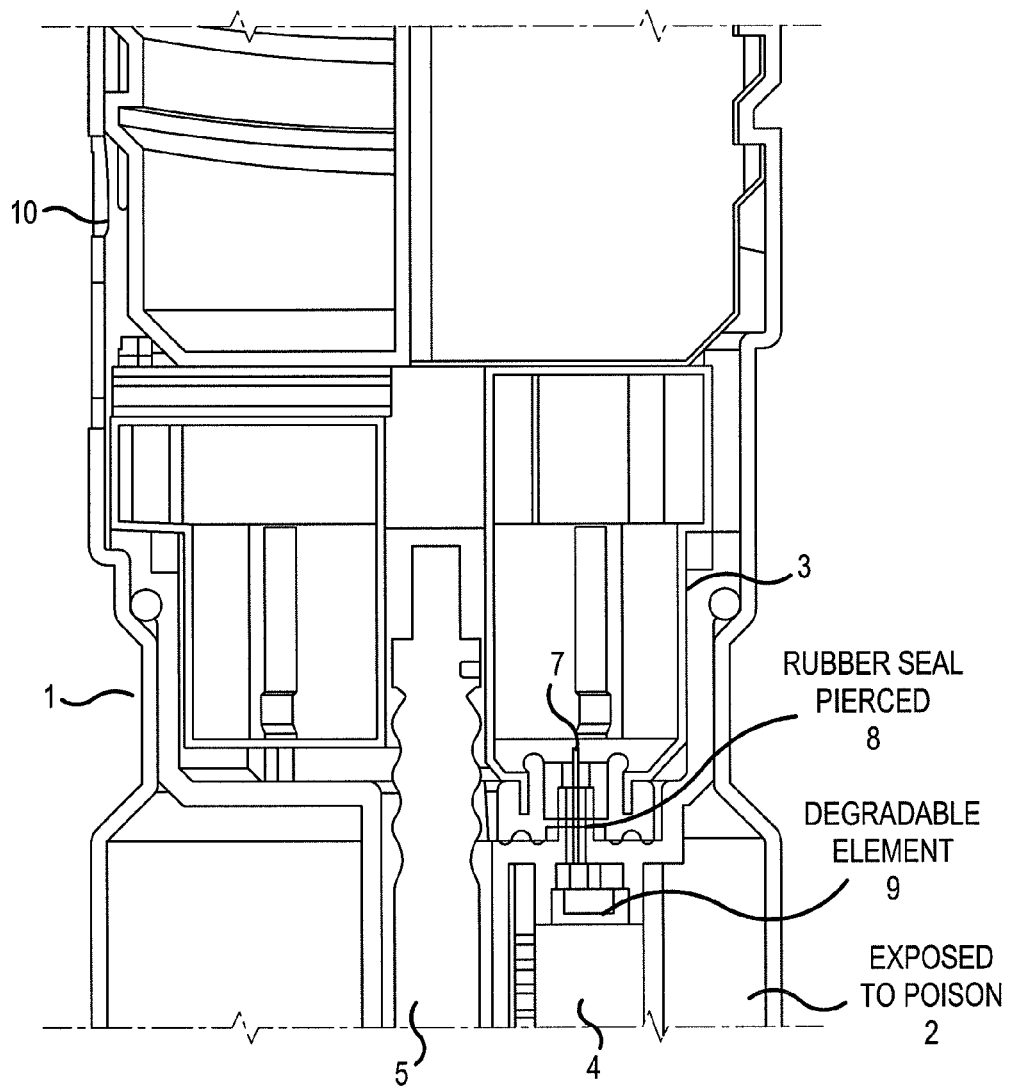

FIGS. 2 and 3 illustrate another embodiment of the present invention. FIG. 2 illustrates an arrangement before release of the deactivating agent and FIG. 3 an arrangement when the deactivating agent is released. The Figures show an exploded view of only a portion of the cartridge.

FIGS. 2 and 3 show an explosive cartridge (1) in the form of an elongate cylinder made of a suitably rigid plastic. The cartridge includes a sealed chamber (2) containing an explosive composition and a further sealed chamber (3) containing a deactivating agent. During storage and transport of the cartridge (1) the deactivating agent and explosive composition remain sealed in their respective chamber (2,3).

The cartridge (1) also includes a small diameter axial channel (4) extending down within the body of the cartridge (1) from the deactivating agent chamber (3) through the explosive composition. This channel is provided off-centre and is distinct from the channel into which a detonator (5) is provided. The walls of the channel (4) may be formed of a porous material that in use will allow deactivating agent to be communicated to the explosive composition and that has sufficient structural rigidity to define a channel adjacent or through the explosive composition.

At the top (entrance) to the channel (4) there is an arrangement that is designed to cause release of deactivating agent from chamber (3) into the channel (4) when the cartridge (1) is to be used. This arrangement includes an elongate element (7) projecting upwardly from the top of the channel (4). This element (7) may be a tube that is adapted at one end to pierce a correspondingly located (rubber) seal (8) provided on the lower end of the deactivating agent chamber (3). The element (7) communicates at its lower end with a seal (9) provided over the entrance to the channel (4). This seal (9) is made of a material that is degradable on contact with the deactivating agent.

Prior to use the seal (8) is in tact and the seal (8) and element (7) are in close proximity to each other. This arrangement is shown in FIG. 2. In use of the cartridge, the deactivating agent chamber (3) is displaced downwards relative to the element (7) and this occurs as a result of engagement of the upper end of the cartridge (1) with an engagement member (10). In the embodiment shown the inner surface of the upper end of the cartridge (1) includes screw threads adapted to engage corresponding screw threads provided on the outer surface of the engagement member (10). The member (10) may be a specially designed cartridge cap or the lower end of another cartridge (1). The action of screwing the member (10) into the top of the cartridge (1) causes the deactivating agent chamber (3) to be displaced downwards. In turn this causes the piercing element (7) to pierce the (rubber) seal (8). Deactivating agent then flows down through the element (7) thereby coming into contact with the degradable seal (9). This is shown in FIG. 3. As already noted, an air inlet or breather tube may be required to ensure flow of the deactivating agent, and surface tension effects may need to be taken into account too. Preferably, the air inlet/breather tube is "activated" only when the member (10) is screwed into the top of the cartridge (1) in order to release the deactivating agent. This prevents leakage of deactivating agent prior to use.

After a predetermined period of time the seal (9) will be dissolved/consumed/weakened by the action of the deactivating agent. The integrity of the seal is lost thereby allowing deactivating agent to drain into the channel (4). The deactivating agent then flows through the porous/permeable walls of the channel and into contact with the explosive composition. The deactivating agent goes on to desensitise the explosive composition thereby rendering it safe.

Figure 4:
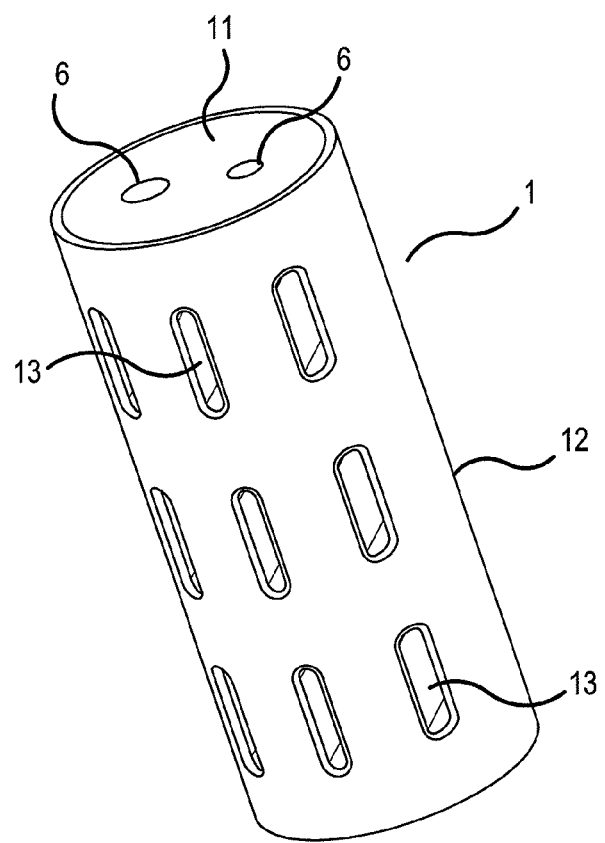
FIGS. 4 and 5 are perspective views of explosive cartridges in accordance with the present invention.

FIG. 4 shows an explosive cartridge (1) useful in implementation of the invention. The cartridge 1 includes explosive composition (11) which typically is in a solid (cast) form, such as Pentolite (typically a PETN/TNT and/or RDX mix). The explosive composition 11 includes the detonator receiving channels (6) that enable the cartridge to be initiated by different sized (diameter) detonators. The cartridge (1) includes an outer shell (12) that is made of a water-permeable or water-degradable material. In the field environmental water will thus permeate or degrade the shell. The shell (12) also defines passages (13) extending into the explosive composition (11). The use of this configuration and type of shell allows environmental water to come into contact with the explosive composition (11), and is thus useful in embodiments of the invention where this is intended/required. The explosive composition (11) includes an enzyme-based deactivating agent. For example, the enzyme may be in contact with and/or distributed throughout the explosive composition (11) in the form of pellets or granules. the pellets/granules may be mixed with the explosives composition (11) before the composition (11) is poured (cast) into the outer shell (12). Additionally or alternatively the enzyme may be provided within the material making up the outer shell (12).

Figure 5:
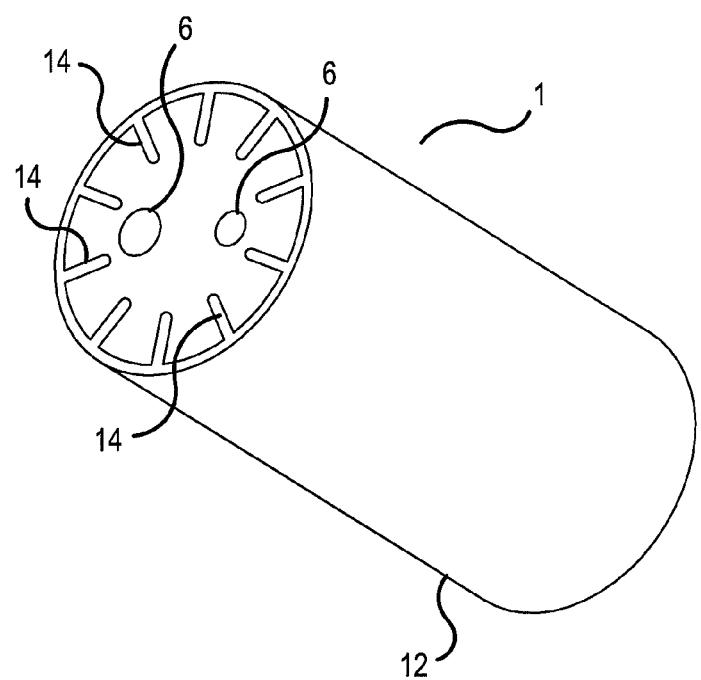

FIG. 5 shows another form of an explosive cartridge (1) useful in implementation of the invention. The cartridge 1 includes an explosive composition 11, such as a cast Pentolite explosive, surrounded by a shell (12). An enzyme as deactivating agent may be provided in the explosive composition as described above in relation to FIG. 4. The shell 12 is water-permeable or water-degradable, as for the shell discussed in FIG. 4. In FIG. 2 the shell 12 includes radial members 14 extending into the bulk of the explosive composition. The intention here is that when the cartridge 1 comes into contact with water, water dissolves the shell (12) so that water is conveyed into contact with and through the explosive composition, as required by certain embodiments of the invention described herein. The rate at which the shell (12) dissolves may be controlled by suitable selection of material used to form the shell (12).

The material making up the shell (12), passages 13 and/or radial members 14 may be formed of a material that may be degraded by the action of microorganisms. As the shell (12) is degraded this allows water present in the environment to contact the deactivating agent provided in the explosive composition (11) or shell (12). In turn this renders the deactivating agent suitably mobile and/or active so that the deactivating agent can commence desensitisation of the explosive composition. The microorganisms may also have the effect of acting on the explosive composition to convert it into less detonable or non-detonable by-products and/or by-products that are more environmentally friendly.

Figure 6:
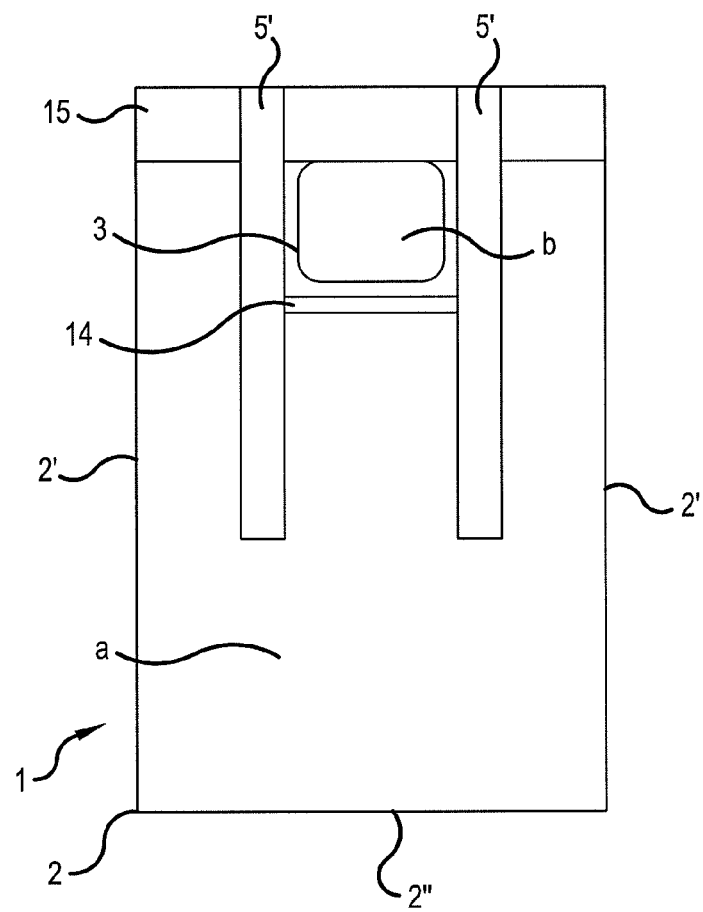
FIG. 6 is a cross-section of an explosives cartridge in accordance with the present invention.

FIG. 6 shows and explosive cartridge (1) suitable for use in seismic exploration. The cartridge (1) includes an explosive composition (a) and deactivating agent (b) in respective chambers (2,3). The chamber for the explosive composition (a) is in the form of a cylindrical shell comprising wall portions (2') sealed by a base (2"). The explosive composition (a) may be Pentolite, possibly in mixture with RDX and/or aluminium particles. The deactivating agent (b) may be a dishwasher detergent containing enzymes and alkaline salts that are capable of deactivating the explosive composition.

The explosive composition (a) and deactivating agent (b) are separated in their respective chambers by a base plate (14) that is loosely fitted at the lower end of the chamber (3) for the deactivating agent (b). The plate (14) may be formed of any suitable material such as a polyester or polycarbonate. The plate (14) may be provided with a double-sided adhesive to allow it to be positioned and retained in place—the purpose of the plate is to prevent contact between the deactivating agent (a) and explosive composition (b). That said, depending upon the nature of the deactivating agent and explosive composition it may be possible to dispense with the plate (14) altogether.

The cartridge (1) also includes two detonator receiving channels (5') extending into the explosive composition (a). The cartridge (1) also includes a cap (15) at one end. This cap (15) is sized and shaped to fit, for example by interference fit, into the shell housing the explosive composition.

Figure 7:
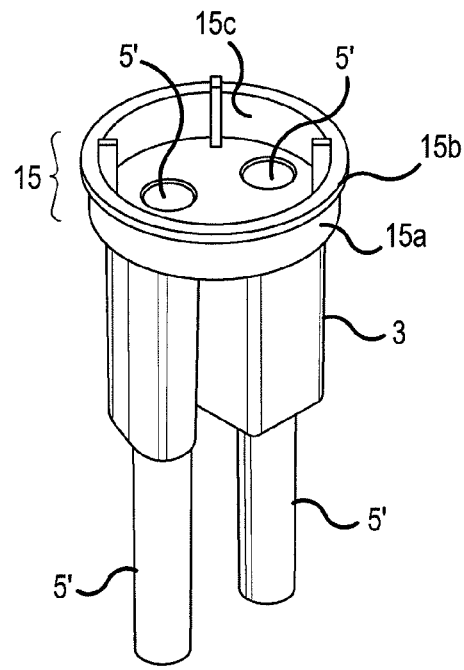
FIGS. 7 and 8 are perspective views showing a component of the explosives cartridge depicted in FIG. 6.
Figure 8:
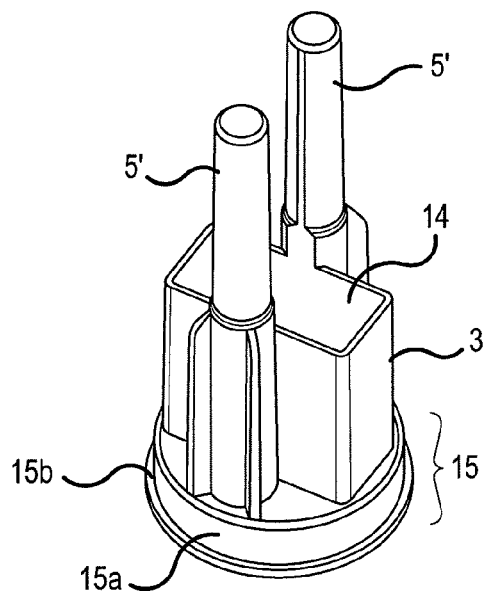

In practice the cartridge (1) may be provided as separate components that are assembled during loading of respective components and when used in the field. With respect to FIG. 6, one component may be integrally formed (by injection moulding of a plastics material) to include and define, the cap (15), the detonator receiving channels (5') and the chamber (3) for the deactivating agent (b) as illustrated in FIGS. 7 and 8. The base plate (14) and chamber/shell (2) for the explosive composition (a) are separate components. The chamber (2) is made up of a cylindrical tube comprising wall portions (2') and a base (2") that is attached at a lower end of the tube thereby sealing it.

FIGS. 7 and 8 illustrate certain components shown in FIG. 6. Thus, FIGS. 7 and 8 show the cap (15), detonating receiving channels (5') and chamber (3) for the deactivating agent formed as a one-piece construction, for example by injection moulding of a suitable plastics material. The chamber (3) for the deactivating agent is sealed by a separate plate (14). The cap (15) comprises a circular wall portion (15a) with a lip (15b) that enables the cap (15) to be secured (by interference fit) into a suitably sized and shaped chamber in which an explosive composition is provided (not shown in FIGS. 7 and 8). The cap (15) is typically inserted into a tube forming. The wall portions (2') extend above and below the cap (15) once inserted and are adapted to allow attachment of other cartridges or a nose cone, for example by thread fitting. The internal surface of the wall portion (2') may include a lug or tab to engage the lip (15b) so as to maintain the cap (15) in position. The upper end of the cap (15) is open to allow for insertion of at least one detonator into respective detonator receiving channels (5'). The end of the cap (15c) may be sealed with a suitably sized and shaped lid (not shown) or be formed in an injection moulding process. The cap (15) and/or wall portions (2') may include apertures to allow water to enter the explosive cartridge. As noted the wall portion (2') extending above the position of the cap (15) may receive the lower end of another explosive cartridge to form a train of cartridges. In this regard a surface (15c) of the wall portion (2') may be threaded to mate with corresponding threads provided on the outer surface and at the base of another cartridge. Cartridges may also be coupled by interference fit or by clip fasteners. The cap (15) may include apertures or grooves (not shown) in the side wall thereof extending through the circular wall portion (15a) and lip (15b) through which detonator leads may be passed after a detonator loading.

The embodiment illustrated in FIGS. 6-8 may be implemented as follows. In the orientation shown in FIG. 8 the plate (14) is removed and deactivating agent inserted into the chamber (3). The plate (14) is then replaced thereby sealing the chamber (3). The seal is loose in the sense that the chamber (3) is not liquid tight. Still in the orientation shown in FIG. 8, a cylindrical tube defining the wall portions (2') of the chamber (2) for the explosive composition (a) is inserted over the cap (15) with the cap (15) being retained in place by interference fit between the wall portion (2') and cap lip (15b).

An explosive composition, such as Pentolite, can then be poured into the open end of the tube, thereby surrounding the chamber (3) and detonator receiving channels (5'). If Pentolite is used it is cast above its melting point and allowed to solidify. Solidification may result in the formation of cracks and fissures extending through the bulk of the explosive composition. This may be desirable as such cracks and fissures allow water to travel through the explosive composition, as may be desired. Once the tube has been suitably filled with explosive composition, and the composition solidified as might be necessary, a base (2") is attached to the open end of the tube. The base (2") and wall portions (2') may form a seal by interference fit, male-female screw threading or by clip fastening.

In use the component so-formed is loaded with one or more detonators with the detonator leads being passed out of the cap (15) or upper part of wall portions (2') as noted. The top end of the cap (15) may itself be sealed using a lid made of water-degradable material (not shown).

In the embodiment described it is intended that the deactivating agent is rendered mobile by water entering the chamber (3) around the edges of the plate (14). The plate may additionally or alternatively include apertures to allow water entry into the chamber (3). Additionally or alternatively, the wall portions of the chamber (3) may also include structures to allow water to enter the chamber (3) (the chamber (3) may itself be made of water-degradable material to facilitate water ingress). Water mobilises the deactivating agent and the mobilised deactivating agent may exit the chamber (3) for contact with explosive composition via the same (or different) route through which water entered the chamber (3).

Water may find its way into the chamber (3) in one or a combination of more than one way, as follows.

Where respective components are joined together, for example the wall portions (2') forming the chamber (2) and the cap (15) or the wall portions (2') and base (2"), the joint may allow water ingress. In this case water would enter the chamber (3) around the plate (14) by migration through the bulk of the explosive composition. The composition must therefore allow water transport by the presence of artificial and/or intrinsic water transport structures.

Additionally or alternatively, water may enter the explosive composition through the walls (2') and/or base (2") of the chamber (2). One or both of these components may include channels/apertures to allow water entry and/or one or both may be water-permeable or water-degradable. The exact configuration will depend upon the form of, and thus the containment needs, of the explosive composition.

Additionally or alternatively, water may enter the chamber (3) via the cap (15). Thus, the cap (15) may include channels/apertures extending through the cap (15) and into the chamber (3), for example through an aperture between the inner surface (15c) and the chamber (3). The aperture may itself be sealed by a water-degradable material. Water may enter the cap (15) through loose fitting seals (between the cap (15) and cap lid or between the wall portion (2') and an adjacent cartridge when a train of multiple cartridges is assembled). The apertures/grooves for the detonator leads may also allow water to enter the cap. Apertures/grooves in the upper part of the wall portions (2') may also allow water ingress.

One or more components of the cartridge may be water-degradable, and the degradability may be selective in order to provide enhanced control with respect to intended deactivation of the explosive composition.

Irrespective of the way in which water enters the chamber (3), when the deactivating agent is mobilised it will exit the chamber (3) and contact the explosive composition, thereby commencing deactivation of the explosive composition.

Embodiments of the present invention are illustrated in the following non-limiting example.

EXAMPLE 1

500 ml of water was heated to 45° C. in a water bath. Pentolite was added to 200 ppm (200 mg/L), consisting of 70 ppm PETN and 130 ppm TNT. Deactivating agent (in the form of commercially available detergent) at the recommended dose rate and at 10× the recommended dose rate was added as noted in Table 1 below. The resultant solution was then removed from the water bath and allowed to sit at room temperature (21° C.) overnight in the dark. Samples were taken and analysed for PETN and TNT. The experiment was repeated using sodium hydroxide and water as controls. The results are presented in Table 1 below. Table 2 below provides a list of ingredients as declared in relevant Material Safety Data Sheets (MSDSs) for the detergents used in the experiments.

TABLE 1

| Reagent | Dose (g/L) | PETN (mg/L) | TNT (mg/L) |
|---|---|---|---|
| BIOZET (standard dose) | 0.417 | 45 | 83 |
| COLD POWER concentrate (standard dose) | 1.67 | 43 | 54 |
| COLD POWER RAINFOREST (standard dose) | 1.67 | 41 | 66 |
| DRIVE concentrate (standard dose) | 1.75 | 49 | 62 |
| DUO MATIC (standard dose) | 3.5 | 50 | 24 |
| DYNAMO MATIC (standard dose) | 3.6 | 43 | 43 |
| FAB concentrate (standard dose) | 1.5 | 43 | 53 |
| FINISH POWERBALL 3 in 1 (standard dose) | 2.1 | 40 | 45 |
| FINISH POWERBALL 5 in 1 (standard dose) | 2.1 | 34 | 56 |
| HOME BRAND 3 in 1 (standard dose) | 2.05 | 37 | 43 |
| MORNING FRESH 5 in 1 (standard dose) | 1.82 | 43 | 75 |
| NAPISAN PLUS (standard dose) | 4 | 48 | 0.2 |
| OMO MATIC (standard dose) | 3.17 | 38 | 35 |
| RADIANT MICRO concentrate (standard dose) | 0.7 | 38 | 88 |
| RADIANT POWER concentrate (standard dose) | 1.58 | 34 | 32 |
| WOOLWORTHS dishwasher tablets 5 in 1 (standard dose) | 2.14 | 37 | 37 |
| WOOLWORTHS laundry powder Advanced (standard dose) | 1.17 | 46 | 64 |
| WOOLWORTHS LAUNDRY powder Front Loader (standard dose) | 2.33 | 39 | 40 |
| SPREE concentrate Apple Fresh (standard dose) | 1.67 | 45 | 35 |
| SQUEEK 4 in 1 (standard dose) | 1.1 | 43 | 14 |
| SURF TROPICAL (standard dose) | 1.5 | 48 | 64 |
| BIOZET (10x dose) | 4.17 | 41 | 11 |
| COLD POWER concentrate (10x dose) | 16.7 | 51 | 3.2 |
| COLD POWER CONCENTRATE (10x dose) | 16.7 | 48 | 8.5 |
| DRIVE concentrate (10x dose) | 17.5 | 48 | 13 |
| DUO MATIC (10x dose) | 35 | 52 | 0.2 |
| DYNAMO MATIC (10x dose) | 36 | 4.4 | 0.5 |
| FAB concentrate (10x dose) | 15 | 40 | 4.7 |
| FINISH POWERBALL 3 in 1 (10x dose) | 21 | 32 | 0.4 |
| FINISH POWERBALL 5 in 1 (10x dose) | 21 | 32 | 1.3 |
| HOME BRAND 3 in 1 (10x dose) | 20.5 | 24 | <0.1 |
| MORNING FRESH 5 in 1 (10x dose) | 18.2 | 29 | 5.7 |
| NAPISAN PLUS (10x dose) | 40 | 51 | <0.1 |
| OMO MATIC (10x dose) | 31.7 | 45 | 2.8 |
| RADIANT MICRO concentrate (10x dose) | 7 | 40 | 36 |
| RADIANT POWER concentrate (10x dose) | 15.8 | 39 | 0.5 |
| WOOLWORTHS dishwasher tablets 5 in 1 (10x dose) | 21.4 | 17 | <0.1 |
| WOOLWORTHS laundry powder Advanced (10x dose) | 11.7 | 42 | 25 |
| WOOLWORTHS laundry powder Front Loader (10x dose) | 23.3 | 28 | 21 |
| SPREE concentrate Apple Fresh (10x dose) | 16.7 | 31 | 0.7 |
| SQUEEK 4 in 1 (10x dose) | 11 | 16 | <0.1 |
| SURF TROPICAL (10x dose) | 15 | 21 | 6.8 |
| Control | — | 45 | 110 |
| 0.004M NaOH control | 0.167 | 40 | 1.0 |

TABLE 2

| Detergent | Ingredients (as per MSDS) Name | Proportion |
|---|---|---|
| BIOZET | No information as yet | |
| COLD POWER | Pentasodium triphosphate | 10-30 |

TABLE 2-continued

| Detergent | Ingredients (as per MSDS) Name | Proportion |
|---|---|---|
| concentrate | Sodium sulphate | 10-30 |
|  | Sodium carbonate | 10-30 |
|  | Sodium tridecyl benzene sulphonate (linear) | 0-10 |
|  | Sodium silicate | 0-5 |
|  | Sodium silicoaluminate | 0-5 |
|  | Non-haz ingredients | to 100 |
| COLD POWER RAINFOREST | Sodium sulphate | 30-60 |
|  | Pentasodium triphosphate | 10-30 |
|  | Sodium silicate | 1-10 |
|  | Tetrasodium pyrophosphate | 0-1 |
|  | Sodium hydroxide | 0-0.1 |
|  | Non-haz ingredients | to 100 |
| DRIVE concentrate | Alkaline salts | 10-30 |
|  | Anionic surfactants | 10-30 |
|  | Enzymes | 0-10 |
|  | Non-haz ingredients | to 100 |
| DUO MATIC | Sodium tripolyphosphate | Proportions not supplied |
|  | Sodium xylene sulphonate |  |
|  | Dodecyl benzene sulphonate |  |
| DYNAMO MATIC | Sodium carbonate | 10-30 |
|  | Ethoxylated C12-C15 alchohol | 0-5 |
|  | Tetrasodium pyrophosphate | 0-1 |
|  | Proteolytic enzyme | 0-0.1 |
|  | Non-haz ingredients | 60-100 |
| FAB concentrate | Sodium carbonate | 30-60 |
|  | Tetrasodium pyrophosphate | 0-1 |
|  | Sodium hydroxide | 0-0.1 |
|  | Non-haz ingredients | 60-100 |
| FINISH POWERBALL 3 in 1 | Sodium tripolyphosphate | 30-60 |
|  | Sodium carbonate | 10-<30 |
|  | Sodium percarbonate | 10-<30 |
|  | Sodium silicate | <10 |
|  | Non-ionic surfactant | <10 |
|  | Proteolytic enzyme | <1 |
|  | Amylase enzyme | <1 |
|  | Non-haz ingredients | to 100 |
| FINISH POWERBALL 5 in 1 | Sodium tripolyphosphate | 30-50 |
|  | Sodium carbonate | 15-30 |
|  | Sodium carbonate peroxyhydrate | 5-15 |
|  | Sodium disilicate |  |
|  | Fatty alcohol alkoxylate (1) | <5 |
|  | Fatty alcohol alkoxylate (2) | <5 |
|  | Proteolytic enzyme | <1 |
|  | Zinc sulphate | <1 |
|  | Amylase enzyme | <0.25 0.1 |
| HOME BRAND 3 in 1 | Sodium carbonate | 10-100 |
|  | Sodium percarbonate | 1-10 |
|  | Sodium silicate | 1-10 |
|  | Alcohols C12-C15 ethoxylated propoxylated | 1-10 |
| MORNING FRESH 5 in 1 | No information as yet |  |
| NAPISAN Plus | Sodium carbonate | 30-60 |
|  | Sodium percarbonate | 10-<30 |
|  | Sodium silicate | <10 |
|  | Anionic surfactant | <10 |
|  | Proteolytic enzymes | <10 |
|  | Non-haz ingredients | to 100 |
| OMO MATIC | Alkali salts | 10-30 |
|  | Enzymes | 0-10 |
|  | Non-haz ingredients | to 100 |
| RADIANT MICRO concentrate | No information |  |
| RADIANT POWER concentrate | No information |  |
| WOOLWORTHS dishwasher tablets 5 in 1 | No information confirmed as yet, however, same MSDS supplied as for Homebrand |  |
| WOOLWORTHS laundry powder Advanced | No information confirmed as yet, however, same MSDS supplied as for Homebrand |  |
| WOOLWORTHS laundry powder Front Loader | No information confirmed as yet, however, same MSDS supplied as for Homebrand |  |
| SPREE concentrate Apple Fresh | Sodium sulphate |  |
|  | Sodium carbonate |  |
|  | Pentasodium triphosphate |  |
|  | Sodium silicate |  |
|  | Tetrasodium pyrophosphate |  |
|  | Sodium hydroxide |  |
|  | Non-haz ingredients |  |
| SQUEEK 4 in 1 | No information as yet |  |
| SURF TROPICAL | Alkali salts | 10-30 |
|  | Non-haz ingredients | to 100 |

Table 1 demonstrates that commercially available washing detergents possess a TNT converting ability. The nature of this conversion may involve, amongst other reactions, chemical reduction of one, or more, of the nitrate groups on the TNT molecule to amines, a well established reaction observed in nature. One result of this conversion of TNT is a loss of part, or all, of the Pentolites explosive potential and a rendering of the device less prone to initiation.

This conversion of TNT may also enhance the biodegradation of the device, due to removal of TNT, a chemical known in the art, to be toxic to living organisms, including soil borne microbes.

This conversion of TNT as demonstrated in Table 1, whilst occurring in the presence of strong base, as shown with the sodium hydroxide control value, is enhanced by the presence of enzymes in the commercial detergent preparations. It is accepted that enzymes accelerate chemical reactions including various conversions of PETN and TNT. It is also known that enzymes possess the potential to interact with chemicals other than their intended, or preferred substrate. One example of this is the action of PETN reductase on TNT, two functionally related, but structurally unrelated compounds.

Thus the ability of non-TNT or PETN specific enzymes contained in detergent formulations including, but not limited to, proteases, amylases, lacasses and other unspecified enzymes, to convert TNT can be explained.

The reference to any prior art in this specification is not, and should not be taken as, an acknowledgment or any form of suggestion that that prior art forms part of the common general knowledge in Australia.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A method of deactivating an explosive composition provided in an explosive cartridge, which method comprises:
    exposing the explosive composition to a deactivating agent that is capable of rendering the explosive composition insensitive to detonation and to another reagent that is capable of rendering the explosive composition insensitive to detonation;
    wherein the deactivating agent is an enzyme used in isolation from any living cell with which it might normally be associated or produced; and
    wherein the deactivating agent and another reagent render the explosive composition insensitive to detonation after a predetermined period of time, with the proviso that said another reagent is other than water.

2. The method of claim 1, wherein the enzyme is present in a laundry or dishwasher detergent.

3. The method of claim 1, wherein the another reagent is one or more of a microorganism, a (non-biological) chemical, and/or a plant or a plant extract/derivative.

4. The method of claim 1, wherein the another reagent is a reagent external to the explosive cartridge that will find its way or be introduced into the cartridge during use thereof.

5. The method of claim 1, wherein the explosive cartridge is designed to allow environmental water to enter the body of the cartridge and contact the explosive composition.

6. The method of claim 1, wherein the explosive composition is provided in a chamber that is adapted to be secured to another component comprising a chamber for the deactivating agent.

7. The method of claim 6, wherein the chamber for the deactivating agent is of single piece construction.

8. The method of claim 1, wherein the deactivating agent is provided separate to the explosive composition and must be mobilised in order for contact with the explosive composition to take place.

9. The method of claim 8, wherein the deactivating agent is provided in any suitable form that is rendered mobile by water that enters or is delivered into the explosive cartridge when used.

10. The method of claim 9, wherein the explosive cartridge includes one or more inlets (apertures) and/or water-degradable pathways to allow environmental water to flow into the cartridge and directly into contact with the deactivating agent.

11. The method of claim 9 or claim 10, wherein the explosive cartridge includes one or more inlets (apertures) and/or water-degradable pathways to allow environmental water to flow into the cartridge and into contact with the deactivating agent through the explosive composition.

12. The method of claim 11, wherein the explosive composition includes channels to allow water to migrate to the deactivating agent.

13. The method of claim 1, wherein the explosive composition comprises Pentolite.

14. The method of claim 1, wherein the another reagent is a (non-biological) chemical.

* * * * *